US012616772B2

(12) United States Patent
Planck et al.

(10) Patent No.: US 12,616,772 B2
(45) Date of Patent: May 5, 2026

(54) TWO-DIMENSIONAL MATERIAL FOR MEDICAL WOUND AREA TREATMENT

(71) Applicant: PolyMedics Innovations GmbH, Denkendorf (DE)

(72) Inventors: Heinrich Planck, Nuertingen (DE); Erhard Mueller, Stuttgart (DE); Svenja Reimer, Aichtal (DE); Christian Planck, Kirchheim (DE)

(73) Assignee: PolyMedics Innovations GmbH, Denkendorf (DE)

( * ) Notice: Subject to any disclaimer, the term of this patent is extended or adjusted under 35 U.S.C. 154(b) by 319 days.

(21) Appl. No.: 18/327,311

(22) Filed: Jun. 1, 2023

(65) Prior Publication Data
US 2023/0302190 A1 Sep. 28, 2023

Related U.S. Application Data

(63) Continuation of application No. PCT/EP2021/084219, filed on Dec. 3, 2021.

(30) Foreign Application Priority Data

Dec. 3, 2020 (DE) ..................... 10 2020 215 320.5

(51) Int. Cl.
*A61L 15/32* (2006.01)
*A61L 15/22* (2006.01)
*A61L 15/42* (2006.01)

(52) U.S. Cl.
CPC ........... *A61L 15/325* (2013.01); *A61L 15/225* (2013.01); *A61L 15/42* (2013.01)

(58) Field of Classification Search
CPC ...... A61L 15/225; A61L 15/26; A61L 15/325; A61L 15/42; A61L 15/425; A61L 15/64; A61L 26/0019; A61L 26/0033; A61L 26/009; A61L 26/0085
See application file for complete search history.

(56) References Cited

U.S. PATENT DOCUMENTS

| | | | |
|---|---|---|---|
| 6,706,058 B2 | 3/2004 | Hierlemann et al. | |
| 7,666,803 B2 * | 2/2010 | Shetty ..................... | B32B 5/024 442/268 |
| 2002/0015724 A1 * | 2/2002 | Yang ..................... | A61L 15/325 424/443 |
| 2002/0028231 A1 * | 3/2002 | Hierlemann ............ | A61L 15/64 424/444 |
| 2015/0017225 A1 | 1/2015 | Hubbell et al. | |

FOREIGN PATENT DOCUMENTS

| | | |
|---|---|---|
| DE | 10 2007 024 220 A1 | 11/2008 |
| EP | 0170979 A2 | 2/1986 |
| JP | 2002-113087 A | 4/2002 |
| JP | 2009-506811 A | 2/2009 |
| JP | 2015-128601 A | 7/2015 |
| WO | 2007/025729 A2 | 3/2007 |
| WO | 2009/130485 A2 | 10/2009 |

OTHER PUBLICATIONS

Chen et al. "The Use of a Novel PLGA Fiber/Collagen Composite Web as a Scaffold for Engineering of Articular Cartilage Tissue with Adjustable Thickness", Journal for Biomedical Material Research, 2003, 1170-1180.

* cited by examiner

*Primary Examiner* — Jeffrey T. Palenik
(74) *Attorney, Agent, or Firm* — Orbit IP, LLP; Marc G. Martino

(57) ABSTRACT

A two-dimensional material for the medical wound area treatment is disclosed. A non-woven fabric consists of resorbable polymer filaments and collagen particles which have a particle size I>80 μm and are disposed on and/or in the non-woven fabric.

19 Claims, 2 Drawing Sheets

TWO-DIMENSIONAL MATERIAL FOR MEDICAL WOUND AREA TREATMENT

CROSS-REFERENCE TO RELATED APPLICATIONS

This continuation application claims priority to PCT/EP2021/084219 filed on Dec. 3, 2021 which has published as WO 2022/117844 A1 and also the German application number 10 2020 215 320.5 filed on Dec. 3, 2020, the entire contents of which are fully incorporated herein with these references.

FIELD OF THE INVENTION

The present invention relates to a two-dimensional material for medical wound area treatment.

BACKGROUND OF THE INVENTION

In medical practice, resorbable two-dimensional materials have become established, which are used, for example, as a skin substitute material in burn wounds or also for the treatment of what is known as degloving, i.e., of avulsion wounds of the skin. Such a two-dimensional material is known, for example, from EP 1 181 941 A2 and is marketed by PolyMedics Innovations GmbH, Germany, under the name Supratel Suprathel® In open wound area treatment, the known resorbable two-dimensional material offers pain-relieving and anti-infectious effects and permits a largely undisturbed formation of granulation tissue with at the same time good mechanical properties. However, the two-dimensional material has only a slow adsorption and absorption capacity of the fluids on wound surfaces that are bloody or wetted with exudate, as a result of which the hemostatic effect of the two-dimensional material is limited.

SUMMARY OF THE INVENTION

It is therefore the object of the invention to specify a two-dimensional material for medical wound area treatment which has improved hemostatic properties.

The object relating to the two-dimensional material is achieved by a two-dimensional material having the features specified in claim 1. Preferred developments of the invention are specified in the dependent claims and in the description.

According to the invention, the two-dimensional material comprises a non-woven fabric made of resorbable polymer filaments, in or on which collagen particles having a particle size of more than 80 µm are arranged. Due to the swelling capacity of fibrillar collagen, i.e., collagen that is intact in its secondary or tertiary structure, the binding of water to the covering membrane can be accelerated and the water binding capacity of the covering membrane per unit area can be increased. In this case, structurally intact collagen is understood in the present application to mean such collagen of which the α and β bands are detectable in SDS-PAGE test. Due to the fact that the collagen particles are anchored in or on the, in turn water-absorbing, highly porous non-woven fabric made of resorbable polymer filaments, excess blood plasma and/or wound exudate can be removed more quickly and more effectively from the wound area in the case of wound area application.

In addition, the highly porous non-woven fabric not least makes it possible to provide particularly rapid bioavailability of the collagen particles of the two-dimensional material.

In the case of wound contact of fibrillar collagen, it is known that the binding of the von Willebrand factor (VWF) to the fibrillar collagen and to the corresponding receptor of the thrombocyte membrane of thrombocytes and the adhesion of thrombocytes is promoted. The emptying of thrombocyte granules (degranulation) can be enhanced, and thus the plasmatic blood clotting (secondary hemostasis) can be triggered or amplified. This is advantageous for accelerated and effective hem ostasis, and is not the case when nanoscale collagen particles are used of which the α- and β bands are no longer detectable in SDS-PAGE test. Overall, the hemostatic properties of the two-dimensional material can be further improved thereby, and a vascularization of the wound area and thus the wound healing overall can be accelerated.

In the case of a correspondingly flexibly deformable design of the two-dimensional material, this can easily be adapted in a simple manner to wound areas of the skin that are regularly difficult to cover, for example in the region of joints.

The collagen particles preferably have a particle size in the range from 80 µm to 500 µm, more preferably in the range from 100 µm to 250 µm, very particularly preferably in the range from 100 µm to 150 µm. It has surprisingly been found in practice that the hemostatic effect of the collagen in situ decreases beyond an average particle size of approximately 500 µm, and the anchoring of the collagen on the non-woven fabric is no longer sufficiently stable relative to the mechanical forces acting during the handling and application of the two-dimensional material. This can result in undesired detachment of the collagen particles from the non-woven fabric. In the case of the particle size between 100 µm to 150 µm, a particularly reliable hemostasis can be achieved.

According to a particularly preferred development of the invention, the two-dimensional material comprises 0.4 to 80 wt. %, preferably 0.5 to 25 wt. %, collagen particles. It should be noted that the improved hemostatic properties of the two-dimensional material provided by the collagen are already achieved at approximately 1 wt. % collagen. In this respect, the two-dimensional material can, in particular, comprise 0.4 to 2 wt. % collagen particles.

According to a preferred development of the invention, at least some of the collagen particles are arranged at least in portions on the surface of the non-woven fabric. The size of the collagen particles alone makes the two-dimensional material more hydrophilic in the region of the collagen particles than in the other surface regions without collagen particles. In the case of this design of the two-dimensional material, a direct bioavailability of the collagen particles and thus a particularly rapid onset of hemostatic effect of the covering membrane during wound application can be achieved. This is also advantageous with regard to a possible intraperitoneal use of the two-dimensional material, for example for preventing adhesion. According to a further embodiment of the two-dimensional material, the collagen particles are all arranged on the surface of the non-woven fabric.

The collagen particles can be produced, in particular, from native collagen of Type I and/or Type III, in particular bovine, porcine or also murine collagen. Such collagen is available on the market in sufficient amounts and in high purity.

According to the invention, the polymer filaments can, in particular, comprise a resorbable polymer, in particular a polymer of at least 2 different monomers (copolymer, ter-polymer, and the like) based on the monomers lactide, glycolide, trimetal carbonate, ε-caprolactone and/or 1,4-dioxan-2-one or polyhydroxybutyrate (PHB) or mixtures of these polymers. As a result, the two-dimensional material can develop an anti-infectious and pain-reducing effect analogously to the two-dimensional material mentioned at the outset, the complete hydrolytic and enzymatic degradability in vivo remaining intact.

According to a preferred embodiment of the invention, the two-dimensional material can have a non-woven fabric comprising polymer filaments of 20 wt. % to 99.5 wt. % copolymer and/or polyhydroxybutyrate, and 0.4 wt. % to 80 wt. % collagen particles having a particle size >80 μm, preferably 0.5 wt. % to 25 wt. % collagen particles, very particularly preferably from 0.5 to 2 wt. % collagen particles. Such a two-dimensional material has a broad clinical field of use, with good hemostatic properties.

According to the invention, the polymer filaments of the non-woven fabric can, in particular, be a terpolymer of 65 to 87 wt. % lactide, 5 to 20 wt. % trimethylene carbonate, and 5 to 20 wt. % ε-caprolactone. The monomers lactide, trimethylene carbonate and ε-caprolactone can be present in the terpolymer, in particular the range of 87/8/5 to 70/20/10 wt. %.

The two-dimensional material preferably has a (nominal) thickness d of 50 to 3000 μm, preferably of 80 to 500 μm, or of 800 to 2500 μm. A lower (nominal) thickness of the two-dimensional material itself allows the covering of wound areas of extremely complex geometry. The resulting limited water binding capacity of the non-woven fabric can be compensated for if necessary by a correspondingly greater proportion by weight of collagen particles. Larger nominal thicknesses of the two-dimensional material, in contrast, enable a particularly large water binding capacity and destines the two-dimensional material for use on strongly bleeding or wet wounds.

Depending on the intended field of application of the two-dimensional material, the non-woven fabric can be produced in different ways. The non-woven fabric can for example be meltblown, i.e., the polymer filaments of the non-woven fabric are produced in what is known as the meltblow method. In this way, filament thicknesses of less than 15 μm can be achieved. Alternatively, the polymer filaments according to the invention can also be produced by means of the electrospinning, which is known per se, or centrifugal spinning. In the two last-mentioned cases, nano-polymer filaments having a filament thickness of a few nanometers can be produced. Alternatively, other known non-woven fabric-forming methods can also be used for producing microfiber or nanofiber non-woven fabrics, such as, for example, spun non-woven fabrics.

During the production of the two-dimensional material, the non-woven fabric is preferably doped with the collagen particles only after it has been produced, since said particles do not withstand the mechanical stresses during the production of the polymer filaments. According to the invention, this can be done by scattering the (preferably dried) collagen particles and subsequent pressing or calendering of the non-woven fabric sprinkled with the collagen particles, or else by way of a wet coating method having subsequent drying of the non-woven fabric coated with the collagen particles. During calendering, the collagen particles applied to the non-woven fabric are pressed with the non-woven fabric, with heat input. In this way, the collagen particles can be anchored in a particularly secure and simple manner on the non-woven fabric.

For the respective wet coating method, the collagen particles are suspended in an aqueous solution. In this case, the suspension of the fibrillar collagen particles must take place very carefully in order not to further damage the collagen particles, directly mechanically or by shear forces, in particular to comminute them further. It is important to maintain the integrity and the desired function of the collagen. Care must therefore be taken to ensure large-scale and structure-preserving suspension of the collagen particles. According to the invention, this can be achieved in particular by dispersing or suspending the collagen particles in a solvent, in particular in the aqueous solution, by stirring for a maximum of two minutes, preferably for a maximum of one minute. In addition, the aqueous solution according to the invention can be enriched with a sugar or even an n-hexane solution can be used to protect the collagen.

Further advantages of the invention can be found in the description and the drawings. The exemplary embodiments shown in the drawing are not to be understood as an exhaustive list but rather have an exemplary character for the description of the invention.

DETAILED DESCRIPTION OF THE PREFERRED EMBODIMENTS

Figure 1:
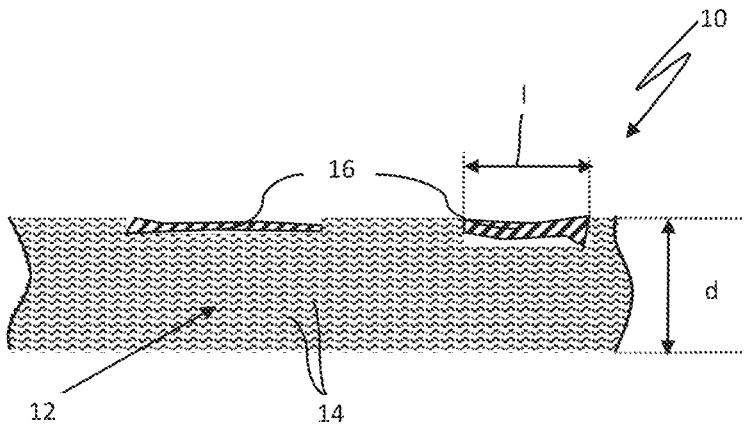
FIG. 1 shows a schematic side view of a two-dimensional material according to the invention for medical wound area treatment, comprising a non-woven fabric made of resorbable polymer filaments and comprising collagen particles having a particle size I>80 μm.

FIG. 1 is a schematic sectional view of a two-dimensional material 10 for medical wound area treatment. The two-dimensional material 10 comprises a non-woven fabric 12 made of resorbable polymer filaments 14. The non-woven fabric 12 has a nominal thickness d which can be from 50 to 3000 μm, preferably from 80 to 500 μm or from 1000 to 2500 μm, depending on the mechanical application requirements placed on the two-dimensional material 10. The non-woven fabric 12 can be produced depending on the desired diameter (not denoted in the drawing) of the polymer filaments 14, by means of what is known as the meltblown method or else by means of electrospinning or centrifugal spinning or other known non-woven formation methods for manufacturing micro- or nanofibers.

The resorbable polymer filaments 14 consist of a resorbable polymer of at least 2 monomers, in particular, a co- or terpolymer based on the monomers lactide, trimethylene carbonate, ε-caprolactone and/or 1,4-dioxan-2-one, polyhydroxybutyrate (PHB) or mixtures of these polymers. The polymer filaments 14 are therefore biocompatible and degradable and completely resorbable in vivo, hydrolytically or by body's own enzymes.

The two-dimensional material further comprises collagen particles 16 having a particle size I of more than 80 μm. The collagen particles 16 are arranged held on or in the non-woven fabric 12 and serve for improved hemostasis or faster absorption of blood and wound fluid. The collagen particles 16 all consist of comminuted native collagen, for example Type I and/or Type III collagen, and can in particular be of bovine, murine or porcine origin. The collagen particles 14 can have a particle size I of between 80 μm and 500 μm, preferably between 100 μm and 500 μm, particularly preferably between 100 μm and 250 μm.

Due to the high porosity inherent to the non-woven fabric, a particularly large and rapid bioavailability of the collagen is ensured, so that its functional advantages can be exhausted at an early stage and comprehensively in wound area treatment. These include, in particular, the known hemostatic properties of fibrillar collagen, its swelling capacity in the case of a pronounced absorption capacity of blood and wound exudate, and the favorable effects thereof with respect to rapid vascularization of the wound area and wound healing. The fibrillar collagen particles 16 of the two-dimensional material thus rapidly extract water from a bleeding wound and thus accelerate the hem ostasis. The combination of the collagen particles 16 and the synthetic resorbable polymer non-woven fabric 12 (e.g., polylactide-caprolactone-trimethylene carbonate) combines the positive properties of both materials. The resorbable polymer filaments 14 of the two-dimensional material 10 have direct contact with the wound (e.g., burn wounds) and can improve wound healing by enzymatic release of lactic acid, and develop pain-relieving and anti-infectious action. In practice, it has been found in this case that even low mass fractions of the collagen particles 14 favor the aforementioned effects. In this respect, the two-dimensional material 10 can comprise between 0.4 and 80 wt. % collagen particles 14, preferably between 0.5 and 25 wt. %, very particularly preferably between 0.4 and 2 wt. % collagen particles 14.

The collagen-containing non-woven fabric 12 is more hydrophilic compared to a structurally identical resorbable non-woven fabric 12 without collagen particles 16, and therefore has less tendency to stick to itself. As a result, the two-dimensional material 10 is easier to handle in clinical practice.

The non-woven fabric 12 can be doped with the collagen particles 16 in different ways. For example, the non-woven fabric may be doped: by sprinkling with collagen particles 16 and calendering under pressure and heat; or by spraying, painting or rolling on a solution with finely dispersed collagen particles 16 and subsequent drying; or by dipping the non-woven fabric 12 into a collagen suspension and subsequent drying.

When manufacturing the two-dimensional material 10, preferably dried native collagen of bovine, porcine or also murine origin is comminuted to collagen particles 14 having a particle size greater than 80 μm, preferably greater than 100 μm.

In a further step, a non-woven fabric made of polymer filaments is produced by means of the meltblow method, electrospinning or centrifugal spinning of a statistical terpolymer of D, l-lactide-trimethylene carbonate-caprolactone.

Example 1—Dry-Coating of the Non-Woven Fabric

Figure 2:
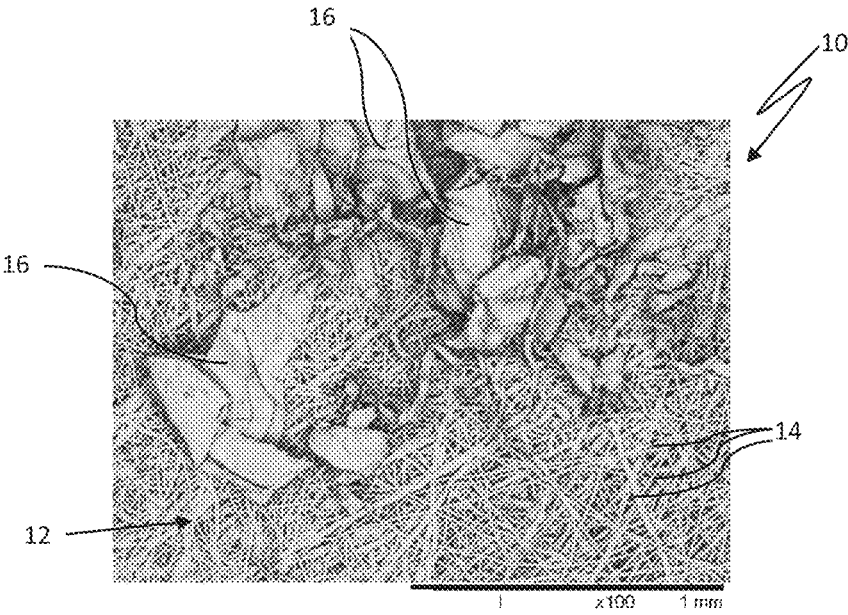
FIG. 2 shows a microscopically enlarged detail view of a two-dimensional material comprising a non-woven fabric and comprising collagen particles, at 250 times magnification.
Figure 3:
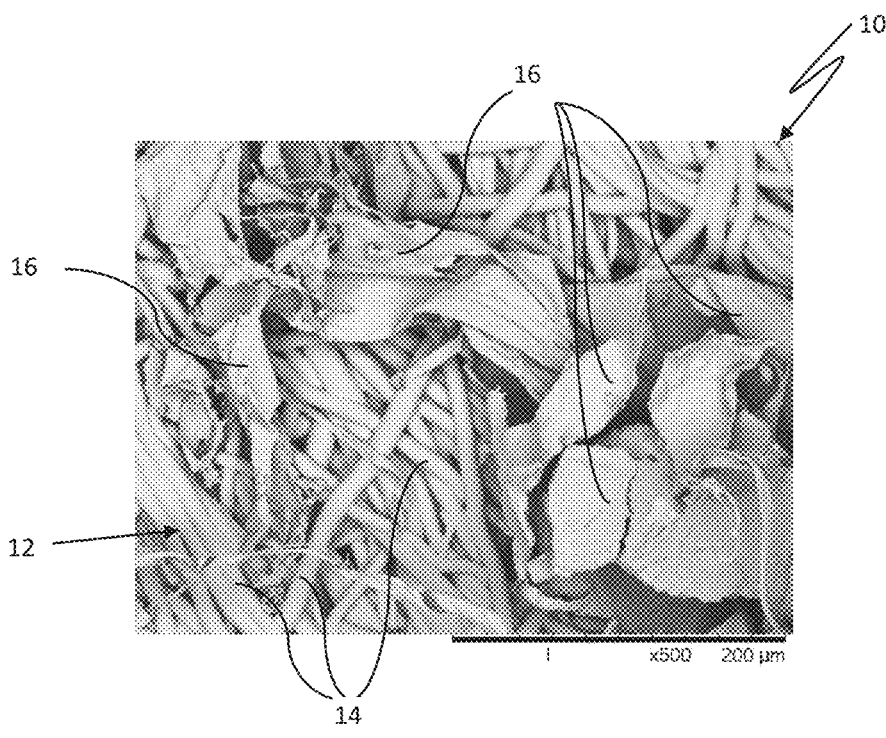
FIG. 3 shows a microscopic, enlarged detail of the two-dimensional material according to FIG. 2, at 500 times magnification.

According to a first embodiment, the collagen particles are scattered onto the non-woven fabric 12 and then pressed with the non-woven fabric 12 at 40° C., 10 bar, for 40 sec. A two-dimensional material 10 in which the non-woven fabric 12 comprises, on its surface collagen particles 16 having a grain or particle size I of >80 μm, is obtained, as shown in FIGS. 2 and 3.

Example 2—Wet-Coating of the Non-Woven Fabric

According to a further embodiment, an aqueous suspension of collagen particles 16 having a particle size >80 μm is provided. Care must be taken here that the size and functionality of the collagen particles 16 are preserved. When the collagen particles 16 are suspended, an extremely gentle, in particular, time-limited stirring is advisable, in order not to further comminute or destroy the collagen particles 16 directly or by shearing. For this purpose, for example a dispersing device of the Ultra Turrax® series from IKA®-Werke GmbH & CO. KG, Germany can be used.

Subsequently, the non-woven fabric 12 is immersed in the aqueous collagen suspension, or the aqueous collagen suspension is sprayed, rolled or painted onto the non-woven fabric 12.

Figure 4:
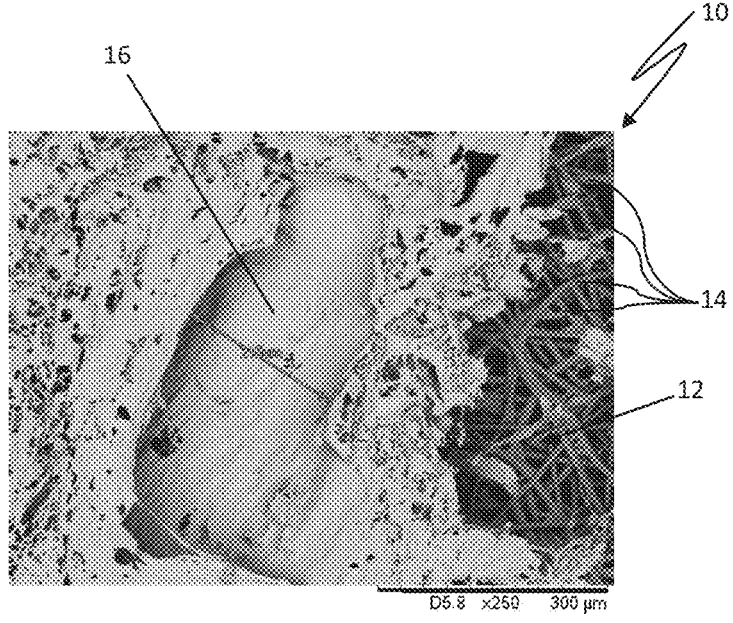
FIG. 4 shows a microscopic, enlarged detail of a two-dimensional material in which the non-woven fabric was calendered after scattering-on of the collagen particles.

Finally, the non-woven fabric 12 doped with the collagen particles 16 is dried, preferably in a vacuum and at room temperature. In this way, a two-dimensional material 10, shown in FIG. 4, is obtained, consisting of a resorbable non-woven fabric 12 comprising collagen particles of >80 μm.

What is claimed is:

1. A method for producing a two-dimensional material for medical wound area treatment, comprising the steps of:
   providing a non-woven fabric made of resorbable polymer filaments;
   providing collagen particles having a particle size I>80 μm;
   scattering the collagen particles onto the non-woven fabric, the collagen particles which are then arranged on and/or in the non-woven fabric; and
   subsequently calendering the non-woven fabric with the collagen particles.

2. The method for producing the two-dimensional material according to claim 1, wherein the collagen particles have an average particle size in the range between 80 μm and 500 μm.

3. The method for producing the two-dimensional material according to claim 1, wherein the collagen particles have an average particle size in the range between 100 μm and 250 μm.

4. The method for producing the two-dimensional material according to claim 1, wherein the collagen particles have an average particle size in the range between 100 μm and 150 μm.

5. The method for producing the two-dimensional material according to claim 1, wherein the two-dimensional material comprises between 0.4 and 80 weight % collagen particles.

6. The method for producing the two-dimensional material according to claim 1, wherein the two-dimensional material comprises between 0.5 and 25 weight % collagen particles.

7. The method for producing the two-dimensional material according to claim 1, wherein the collagen particles are arranged on the surface side of the non-woven fabric.

8. The method for producing the two-dimensional material according to claim 1, wherein the collagen particles are produced from native, bovine, Type I and/or Type III collagen.

9. The method for producing the two-dimensional material according to claim 1, wherein the polymer filaments comprise: a polymer selected from the group consisting of the monomers lactide, trimethylene carbonate, glycolide, ¿-caprolactone and/or 1,4-eioxan-2-one, or polyhydroxybutyrate (PHB); or a mixture of these polymers.

10. The method for producing the two-dimensional material according to claim 9, wherein the polymer comprises copolymers and terpolymers.

11. The method for producing the two-dimensional material according to claim 9, wherein the polymer filaments comprise a terpolymer of 65 to 87 weight % lactide, 5 to 20 weight % trimethylene carbonate and 5 to 20 weight % ε-caprolactone.

12. The method for producing the two-dimensional material according to claim 11, wherein the monomers lactide, trimethylene carbonate and ε-caprolactone are present in the terpolymer in the range of 87/8/5 to 70/20/10 weight %.

13. The method for producing the two-dimensional material according to claim 1, wherein the two-dimensional material has a nominal thickness of 50 μm to 3000 μm.

14. The method for producing the two-dimensional material according to claim 1, wherein the two-dimensional material has a nominal thickness of 80 μm to 500 μm.

15. The method for producing the two-dimensional material according to claim 1, wherein the two-dimensional material has a nominal thickness of 1000 μm to 2500 μm.

16. The method according to claim 1, wherein calendering the non-woven fabric with the collagen particles is done with a heat input.

17. The method according to claim 1, wherein the method to produce the two-dimensional material does not include a wet coating.

18. A method for producing a dry two-dimensional material for medical wound area treatment, comprising the steps of:

providing a non-woven fabric made of resorbable polymer filaments;

providing collagen particles having a particle size I>80 μm;

suspending the collagen particles in an aqueous solution forming a collagen suspension;

subsequently applying the collagen suspension to the non-woven fabric; and subsequently drying the non-woven fabric with the collagen suspension.

19. The method for producing the two-dimensional material according to claim 18, in which a sugar for stabilizing the collagen particles is added to the solution, or an n-hexane solution is used.

\* \* \* \* \*